United States Patent [19]

Barbier et al.

[11] Patent Number: 4,876,247

[45] Date of Patent: Oct. 24, 1989

[54] METHLENEDIPHOSPHONIC ACID DERIVATIVES, AND ANTIRHEUMATIC PHARMACEUTICAL COMPOSITION IN WHICH THEY ARE PRESENT AND METHODS OF USING SAME

[75] Inventors: Alain Barbier, St-Clement la Riviere; Jean-C aude Breliere, Montpellier; Georges Garcia, St-Gely-du-Fesc, all of France

[73] Assignee: Sanofi, Paris, France

[21] Appl. No.: 115,615

[22] Filed: Oct. 30, 1987

Related U.S. Application Data

[63] Continuation of Ser. No. 919,571, Oct. 15, 1986, abandoned, which is a continuation of Ser. No. 691,893, Jan. 16, 1985, abandoned.

[30] Foreign Application Priority Data

Jan. 26, 1984 [FR] France ............... 8401214

[51] Int. Cl.$^4$ ............... C07F 9/38; C07F 9/58; C07F 9/65; A61K 31/44
[52] U.S. Cl. ........................... 514/89; 514/91; 514/114; 546/24; 549/5; 549/7; 544/3; 544/54
[58] Field of Search ............ 546/24; 260/502.5 C; 549/5, 7; 544/3, 54, 57; 514/89, 114, 91

[56] References Cited

U.S. PATENT DOCUMENTS

| | | | |
|---|---|---|---|
| 3,846,420 | 11/1974 | Wollmann et al. | 544/157 |
| 3,962,432 | 6/1976 | Schmidt-Dunker | 514/129 |
| 4,006,182 | 2/1977 | Ploger et al. | 260/502.5 C |
| 4,100,167 | 7/1978 | Selvarajan et al. | 546/22 |

FOREIGN PATENT DOCUMENTS

| | | | |
|---|---|---|---|
| 0015370 | 9/1980 | European Pat. Off. | 260/932 |
| 0098567 | 1/1984 | European Pat. Off. | 260/932 |
| 2754821 | 6/1979 | Fed. Rep. of Germany | 260/502.5 C |

*Primary Examiner*—Alan L. Rotman
*Attorney, Agent, or Firm*—Stevens, Davis, Miller & Mosher

[57] ABSTRACT

The invention relates to methylenediphosphonic acid derivatives of the formula:

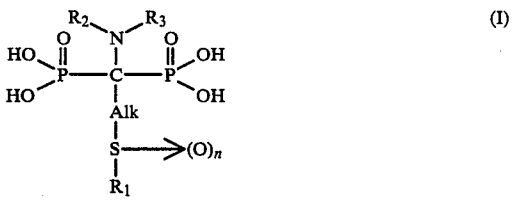

in which:
$R_1$ represents:
  a $C_1$–$C_6$ alkyl group,
  a $C_5$–$C_7$ cycloalkyl group,
  a phenyl group optionally monosubstituted or polysubstituted by a halogen, a $C_1$–$C_6$ alkyl group or a trifluoromethyl group, or
  a 5-membered or 6-membered heterocycle containing 1 or 2 heteroatoms chosen from nitrogen and sulfur,
Alk denotes a linear or branched $C_1$–$C_6$ alkylene group,
$R_2$ represents hydrogen, a $C_1$–$C_6$ alkyl group or a —CONH$_2$ group,
$R_3$ represents hydrogen, a $C_1$–$C_6$ alkyl group, a benzyl group or a phenyl group optionally substituted by chlorine or methyl groups; or alternatively
$R_2$ and $R_3$, taken together, represent a $(CH_2)_m$ group, in which m=4 or 5, and finally
n represents 0 or the integer 1 or 2.

These derivatives possess antirheumatic properties.

8 Claims, No Drawings

METHLENEDIPHOSPHONIC ACID DERIVATIVES, AND ANTIRHEUMATIC PHARMACEUTICAL COMPOSITION IN WHICH THEY ARE PRESENT AND METHODS OF USING SAME

This application is a continuation of application Ser. No. 919,571, filed Oct. 15, 1986, abandoned, which in turn is a continuation of application Ser. No. 691,893, filed Jan. 16, 1985, now abandoned.

The present invention relates to new methylenediphosphonic acid derivatives possessing therapeutic properties enabling them to be used in the treatment of rheumatic manifestations.

More precisely, the compounds according to the invention correspond to the general formula: in which:

$$\begin{array}{c} R_2 \quad R_3 \\ HO \quad O \quad N \quad O \\ \phantom{HO}\diagdown \|\phantom{O} |\phantom{O} \|\diagup \\ \phantom{HOO}P\text{---}C\text{---}P \\ HO\diagup \phantom{\|} | \phantom{\|} \diagdown OH \\ \phantom{HOOOO} Alk \\ \phantom{HOOOO} | \\ \phantom{HOOOO} S\text{---}\!\!\!\!\rightarrow\!\!(O)_n \\ \phantom{HOOOO} | \\ \phantom{HOOOO} R_1 \end{array} \quad (I)$$

in which:
$R_1$ represents:
 a $C_1$-$C_6$ alkyl group,
 a $C_5$-$C_7$ cycloalkyl group,
 a phenyl group optionally monosubstituted or polysubstituted by a halogen, a $C_1$-$C_6$ alkyl group or a trifluoromethyl group, or
 a 5-membered or 6-membered heterocycle containing 1 or 2 hereoatoms chosen from nitrogen and sulfur,
Alk denotes a linear or branched $C_1$-$C_6$ alkylene group,
$R_2$ represents hydrogen, a $C_1$-$C_6$ alkyl group or a —$CONH_2$ group,
$R_3$ represents hydrogen, a $C_1$-$C_6$ alkyl group, a benzyl group or a phenyl group optionally substituted by chlorine or methyl groups; or alternatively
$R_2$ and $R_3$, taken together, represent a $(CH_2)_m$ group, in which $m=4$ or 5, and finally
n represents 0 or the integer 1 or 2.

The acids of the formula (I) are capable of yielding salts with inorganic or organic bases. These salts form an integral part of the invention. One of the compounds of the formula (I) has already been described, but in no case have its therapeutic properties been mentioned.

Thus, West German Patent No. 2,754,821 describes the compound of the formula (I) in which $R_1=CH_3$, $n=0$, Alk is —$CH_2$—$CH_2$— and $R_2=R_3=H$. The said patent also claims the corresponding alkali metal and alkaline earth metal salts as well as the use of the products as additives in the treatment of water in the textile and paper industries.

The other compounds (I) are new.

The present invention also includes a process for the preparation of the compounds of the formula (I). In the case of the compounds (I) in which $R_2=R_3=H$, a nitrile $$\begin{array}{c} R_1S\text{—Alk—CN,} \\ | \\ (O)_n \end{array}$$

in which $R_1$, Alk and n have the meaning defined above, is used as the starting material.

These compounds are prepared by known methods, either by reacting an alkali metal cyanide with an ω-brominated alkylmercaptan or $$\begin{array}{c} (R_1S\text{—Alk—Br),} \\ | \\ (O)_n \end{array}$$

by reacting a ω-halogenated nitrile with a thiol in the presence of an inorganic base.

In the case where $n=0$ and Alk is —$CH_2$—$CH_2$—, a variant of the process consists in reacting the thiol $R_1SH$ with acrylonitrile, in the presence of an organic base, according to the process described by C. D. Hurd and L. L. Gershbein (J. Amer. Chem. Soc. 69, 2328, 1947).

The nitrile prepared in this way is then heated in the presence of phosphorous acid, at a temperature of between 140° C. and 200° C., for a period ranging from 1 hour to a few hours.

A variant of this process consists in adding the nitrile to a solution of phosphorus tribromide in a suitable solvent such as dioxane, in the presence of the stoichiometric quantity of water. The temperature of the medium can vary from case to case between 20° C. and 70° C. The mixture is then stirred for a time varying from a few hours to 1 day, at a temperature varying between 30° C. and 70° C.

Irrespective of the meanings of the substituents $R_2$ and $R_3$, it is also possible to prepare the compounds (I) from the amides $$\begin{array}{c} \phantom{R_1\text{—S—Alk—}}\phantom{C}\phantom{\text{—N}}\diagup^{R_2} \\ R_1\text{—S—Alk—C—N} \quad \text{as starting} \\ | \quad\quad\quad\quad \| \quad\quad \diagdown_{R_3} \\ (O)_n \quad\quad O \end{array}$$

materials, in which formula $R_1$, $R_2$, $R_3$, Alk and n are as defined above.

These amides are obtained in a known manner from the acids $$\begin{array}{c} R_1\text{—S—Alk—COOH,} \\ | \\ (O)_n \end{array}$$

for example by reacting thionyl chloride or phosphorus trichloride with the acid, followed by reaction with the amine $$\begin{array}{c} \phantom{HN}\diagup^{R_2} \\ HN \\ \phantom{HN}\diagdown_{R_3} \end{array}.$$

The amide prepared in this way is then heated with phosphorous acid and phosphorus trichloride in an inert solvent such as dimethoxyethane, at a temperature of between 50° and 100° C., for 2 to 6 hours.

The phosphonic acids thus obtained can be converted to one of their salts in a known manner. The operation is carried out in a hot solvent so that the salt crystallizes on cooling, after the addition of an auxiliary solvent if necessary.

The examples which follow are given in order to illustrate the invention.

EXAMPLE 1

Tetrasodium salt of 1-amino-2-(4-methylphenylthio)ethylidene-1,1-diphosphonic acid dihydrate (SR 42710).

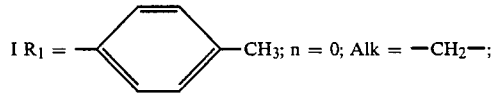

$R_2 = R_3 = H$ (a) 4-Methylphenylthioacetonitrile prepared by the method described by A.A. SANTILLI (C.A. 75 P 5935 S).

(b) 1-Amino-2-(4-methylphenylthio)ethylidene-1,1-diphosphonic acid.

40 g of 4-methylphenylthioacetonitrile are added at 30° C. to a solution of 133 g of phosphorus tribromide in 150 ml of dioxane and the reaction is allowed to proceed for 30 minutes, with stirring. 27 g of water are then added dropwise, the reaction medium being cooled so that the temperature does not exceed 70° C. After a reaction time of 3 hours at 70° C., the dioxane is partially concentrated and the product is precipitated by adding water. After the precipitate has been filtered off and washed with water and then acetone, it is dried. A solution of 5 g of the previous product and 2.5 g of sodium hydroxide in 100 ml of distilled water is heated under reflux for 5 minutes. The solution is filtered hot and the cooled to 50° C.; 100 ml of methanol are then added and the mixture is allowed to cool. The precipitate is filtered off, washed with methanol and then dried at 80° C. in vacuo. This gives 4.8 g of the tetrasodium salt of 1-amino-2-(4-methylphenylthio)ethylidene-1,1-diphosphonic acid; melting point >300° C.

| Elemental analysis with 2 molecules of water | | | | | | | | | |
|---|---|---|---|---|---|---|---|---|---|
| Calculated | C% | 23.95 | H% | 3.35 | N% | 3.10 | S% | | 7.10 |
| Found | | 23.67 | | 3.28 | | 3.06 | | | 6.83 |

EXAMPLE 2

Tetrasodium salt of 1-amino-3-(3-trifluoromethylphenylthio)propylidene-1,1-diphosphonic acid trihydrate (SR 42707 A).

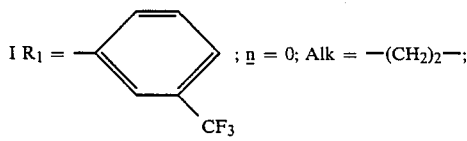

$R_2 = R_3 = H$ (a) 3-(3-Trifluoromethylphenylthio)propionitrile.

48 ml of acrylonitrile are added dropwise to a solution of 61 g of 3-trifluoromethylthiophenol and 2 ml of piperidine, the temperature of the reaction medium being kept below 20° C. The mixture is left to stand for 48 hours and then taken up with 300 ml of ether. After the ether solution has been washed with water and then dried, it is concentrated. This gives an oil, which is chromatographed on silica (230–400 mesh). The fraction eluted with a 90/10 mixture of hexane and acetone yields the expected product in the form of an oil (21 g), which is characterized in thin layer chromatography on silica (eluent: isopropyl ether) by an Rf of 0.6.

(b) Tetrasodium salt of 1-amino-3-(3-trifluoromethylphenylthio)propylidene-1,1-diphosphonic acid trihydrate.

10.5 g of the previous nitrile are added dropwise, at a temperature not exceeding 70° C., to a solution of 25 g of phosphorus tribromide in 40 ml of dioxane. The mixture is subsequently heated for 3 hours at 80° C. and then cooled and 150 ml of water are added. The insoluble material is filtered off, washed with ethyl ether and then with acetone and finally dried in vacuo. The dried precipitate is dissolved in a solution of 500 mg of sodium hydroxide in 15 ml of water; the resulting solution is filtered and 50 ml of methanol are then added. The precipitate obtained is filtered off and washed with methanol and then with ether to give 1.5 g of the expected salt after drying. Melting point >300° C.

| Elemental analysis with 3 molecules of water | | | | | | |
|---|---|---|---|---|---|---|
| Calculated | C% | 22.48 | H% | 3.01 | N% | 2.62 |
| Found | | 22.21 | | 2.38 | | 2.33 |

EXAMPLE 3

1-Amino-3-(3,4-dichlorophenylthio)propylidene-1,1-diphosphonic acid monohydrate (SR 42683).

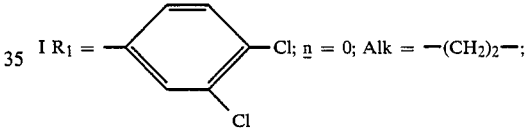

$R_2 = R_3 = H$ (a) 3-(3,4-Dichlorophenylthio)propionitrile.

10 g of 3,4-dichlorothiophenol are added to a solution of 0.2 ml of piperidine in 4 ml of acetonitrile. The mixture is subsequently stirred for 20 hours at 20° C. and then distilled under 0.2 mm of mercury. 12 g of the expected product, distilling at between 138° C. and 142° C., are collected in the form of a colorless oil. This is characterized in thin layer chromatography on silica (silica gel 60 F 54: Merck), with isopropyl ether as the eluent, by an Rf of 0.53.

(b) 1-Amino-3-(3,4-dichlorophenylthio)propylidene-1,1-diphosphonic acid monohydrate.

12 g of the previous nitrile are added at 20° C., over a period of 1 minute, to a solution of 10 ml of phosphorus tribromide in 18 ml of dioxane. The mixtures is subsequently stirred for 20 hours at ambient temperature and 5.5 ml of distilled water are then added, the temperature being kept at 30° C. The mixture is then heated for 3 hours at 60° C. When cooled, it is taken up with 200 ml of acetone to which 10 ml of water are then added. The precipitate formed is filtered off, washed with acetone and then with ether and dried. This gives 11.5 g of the expected product. Melting point: 260°–261° C. (dry).

| Elemental analysis with 1 molecule of water | | | | | | |
|---|---|---|---|---|---|---|
| Calculated | C% | 26.10 | H% | 3.65 | N% | 3.38 |

| -continued |
| Elemental analysis with 1 molecule of water | | | |
|---|---|---|---|
| Found | 25.3 | 3.26 | 3.58 |

EXAMPLE 4

Tetrasodium salt of 1-amino-3-(3,4-dichlorophenylthio)propylidene-1,1-disphosphonic acid monohydrate (SR 42683 A).

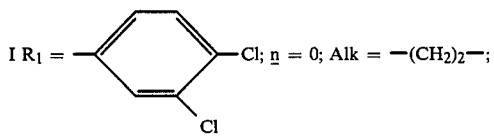

$R_2 = R_3 = H$ 11.4 g of the acid prepared in Example 3 (SR 42683) are treated at 50° C. with a solution of 4.6 g of sodium hydroxide in 125 ml of water. After the acid has completely dissolved, 300 ml of methanol are added. The precipitate is filtered off and washed with methanol and then with ether to give 12.6 g of the expected tetrasodium salt after drying in vacuo at 80° C. Melting point >300° C.

| Elemental analysis with 1 molecule of water | | | | | | |
|---|---|---|---|---|---|---|
| Calculated | C% | 21.52 | H% | 2.21 | N% | 2.79 |
| Found | | 21 | | 2.41 | | 2.51 |

EXAMPLE 5

Tetrasodium salt of 1-amino-4-phenylthiobutylidene-1,1-diphosphonic acid trihydrate (SR 42718 A).

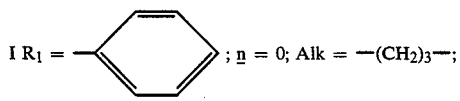

$R_2 = R_3 = H$ (a) 4-Phenylthiobutyronitrile prepared by the method described by J. W. Lynn (C.A. 56, 11441 e).

(b) Tetrasodium salt of 1-amino-4-phenylthiobutylidene-1,1-diphosphonic acid trihydrate.

15.8 g of 4-phenylthiobutyronitrile are added dropwise at 20° C., over a period of 2 minutes, to a solution of 18 ml of phosphorus tribromide in 25 ml of dioxane. After 12 hours at 20° C., 10 ml of distilled water are added, the temperature being kept at 0° C., and the mixture is then heated at 50°-60° C., for 3 hours. 100 ml of water are subsequently added and the precipitate formed is filtered off, washed with water, acetone and finally methanol and then dried in vacuo. After drying, the product is taken up with a solution of 8.5 g of sodium hydroxide in 100 ml of water.

After the product has completely dissolved, 200 ml of methanol are added to the mixture. The precipitate formed is filtered off, washed with methanol and then dried at 80° C. in vacuo. This gives 17.9 g of the expected product. Melting point >300° C.

| Elemental analysis with 3 molecules of water | | | | | | | |
|---|---|---|---|---|---|---|---|
| Calculated | C% | 24.85 | H% | 3.96 | N% | 2.89 | |
| Found | | 24.42 | | 3.92 | | 2.88 | |

EXAMPLE 6

Tetrasodium salt of 1-amino-4-(4-chlorophenylthio)butylidene-1,1-diphosphonic acid (SR 42509 A).

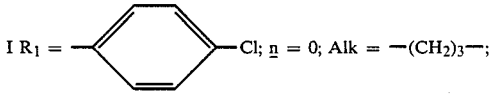

$R_2 = R_3 = H$ (a) 4-(4-Chlorophenylthio)butyronitrile.

44 g of 4-chlorothiophenol are added to a solution of 4 g of sodium in 200 ml of methanol. After heating under reflux for 5 minutes, 32 g of 4-chlorobutyronitrile are added cautiously. The mixture is subsequently heated under reflux for 3 hours and the solution is then cooled and concentrated in vacuo. The residue is taken up with 300 ml of isopropyl ether. The solution is washed with water, dried and then concentrated. The residue is distilled and the fraction distilling at between 150° and 155° C. under 0.03 mm of mercury is separated off. This gives 53.5 g of the expected nitrile in the form of a colorless oil, which is characterized by an Rf of 0.64 in thin layer chromatography on silica gel (silica gel 60 F 54: Merck) with isopropyl ether as the eluent.

(b) Tetrasodium salt of 1-amino-4-(4-chlorophenylthio)butylidene-1,1-diphosphonic acid.

21.1 g of 4-(4-chlorophenylthio)butyronitrile are added to a solution of 19.6 ml of phosphorus tribromide in 30 ml of dioxane over a period of 5 minutes, the temperature being kept at 30° C. The mixture is subsequently stirred for 20 hours at 30° C. and then for 2 hours at 45° C. 50 ml of water are then added, the temperature being allowed to rise to 80° C. The precipitate formed is filtered off, washed with dioxane and then taken up with 100 ml of water. The mixture is heated under reflux for 1 hour and, after cooling, the insoluble material is filtered off, washed with absolute alcohol and finally taken up with 100 ml of a 5% solution of sodium hydroxide. After the solid has totally dissolved, 500 ml of methanol are added. The precipitate formed is filtered off, washed with methanol and dried to give 12.5 g of the expected product. Melting point >300° C.

| Elemental analysis | | | | |
|---|---|---|---|---|
| Calculated | C% | 25.90 | N% | 3.02 |
| Found | | 26.25 | | 3.10 |

EXAMPLE 7

Tetrasodium salt of 1-amino-4-cyclohexylthiobutylidene-1,1-diphosphonic acid monohydrate (SR 42684 A).

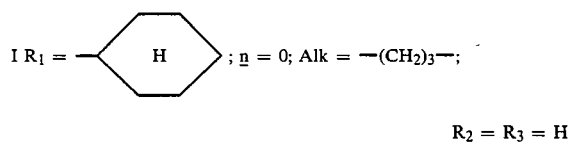

I $R_1 =$ <cyclohexyl>H ; $n = 0$; Alk $= -(CH_2)_3-$;

$R_2 = R_3 = H$ (a) 4-Cyclohexylthiobutyronitrile.

18 g of cyclohexanethiol are added to a solution of 3.5 g of sodium in 75 ml of methanol. The mixture is stirred at 20° C. for 1 hour, 14.2 ml of 4-chlorobutyronitrile are then added and the mixture is heated under reflux for 3 hours before being concentrated in vacuo. The residue is taken up with 300 ml of ether; the solution is washed with water and then dried and concentrated. The residue, distilled under a vacuum of 0.03 mm of mercury, yields 20.8 g of a colorless oil distilling at between 120° and 125° C. The 4-cyclohexylthiobutyronitrile prepared in this way is characterized by an Rf of 0.70 in thin layer chromatography on silica (silica gel 60 F 54: Merck), isopropyl ether being used as the eluent.

(b) Tetrasodium salt of 1-amino-4-cyclohexylthiobutylidene-1,1-diphosphonic acid monohydrate.

A mixture of 11 g of phosphorous acid and 10 g of 4-cyclohexylthiobutyronitrile is heated at 160° C. for 3 hours. The residue is taken up with 40 ml of water; the yellow solid which then crystallizes is washed with water, then with acetone and finally with ether. This compound is taken up with a solution of 1.5 g of sodium hydroxide in 70 ml of distilled water. The mixture is heated at 50° C., with stirring, until the compound has totally dissolved; the solution is allowed to cool and 250 ml of methanol are added. The colorless precipitate obtained is filtered off, washed with methanol and then dried at 80° C. under 0.1 mm of mercury. Melting point >300° C.

| Elemental analysis with 1 molecule of water | | | | | | |
|---|---|---|---|---|---|---|
| Calculated | C% | 26.49 | H% | 4.67 | N% | 3.08 |
| Found | | 25.93 | | 4.90 | | 3.04 |

EXAMPLE 8

Disodium salt of 1-amino-5-(pyridin-2-ylthio)pentylidene-1,1-diphosphonic acid (SR 42709 A).

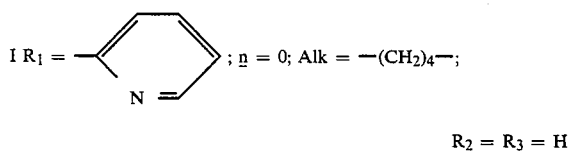

I $R_1 =$ <pyridyl> ; $n = 0$; Alk $= -(CH_2)_4-$;

$R_2 = R_3 = H$ (a) 5-(Pyridin-2-ylthio)valeronitrile 10 g of 2-mercaptopyridine and 20 g of 6-bromovaleronitrile are added successively to a solution of 2.26 g of sodium in 200 ml of methanol. After heating under reflux for 3 hours, the mixture is concentrated in vacuo. The residue is taken up with 200 ml of ether. The solution is washed with water and then dried and concentrated; this gives 15 g of the expected nitrile, which is characterized by an Rf of 0.39 in thin layer chromatography on silica (silica gel 60 F 54: Merck) with isopropyl ether as the eluent.

(b) Disodium salt of 1-amino-5-(pyridin-2-ylthio)pentylidene-1,1-diphosphonic acid.

A mixture of 10.2 g of 5-(pyridin-2-ylthio)valeronitrile and 12 g of phosphorous acid is heated at 150° C. for 1 hour and then at 170° C. for 3 hours. After cooling, the mixture is taken up with 100 ml of water, and 2.5 g of sodium acetate are added. The medium is then extracted twice with ether and the aqueous phase is separated off; 300 ml of methanol are added to the latter; the precipitate formed is filtered off, washed with methanol and then with ether and finally recrystallized from a 60/40 mixture of water and methanol. This gives 4.2 g of the expected product. Melting point >300° C.

| Elemental analysis | | | | | | |
|---|---|---|---|---|---|---|
| Calculated | C% | 30.00 | H% | 4.03 | N% | 7.00 |
| Found | | 30.00 | | 4.20 | | 7.02 |

EXAMPLE 9

Disodium salt of 1-amino-6-propylthiohexylidene-1,1-diphosphonic acid (SR 42708 A).

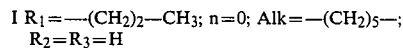

I $R_1 = -(CH_2)_2-CH_3$; $n = 0$; Alk $= -(CH_2)_5-$;
$R_2 = R_3 = H$ (a) 1-Cyano-5-propylthiopentane.

26 g of propanethiol and then 45 g of 1-cyano-5-bromopentane are added successively to a solution of 8 g of sodium in 600 ml of ethanol. After heating under reflux for 6 hours, the solvent is concentrated and the residue is then taken up with 500 ml of water and extracted with ether. After chromatography on a column of silica (230-240 mesh), the concentrated organic phase yields 28 g of the expected nitrile, which is characterized by its Rf of 0.60 in thin layer chromatography on silica gel (silica gel 60 F 54: Merck) with isopropyl ether as the eluent (Rf=0.10 with a 1/9 mixture of acetone and hexane as the eluent).

(b) Disodium salt of 1-amino-6-propylthiohexylidene-1,1-diphosphonic acid.

A solution of 17.5 g of 1-cyano-5-propylthiopentane and 20 g of phosphorous acid is heated at 150° C. for 1 hour and then at 180° C. for 2 hours. After cooling, the precipitate is taken up in acetone, filtered off and then dried. It is then taken up with a solution of 40 g of sodium acetate in 400 ml of water. The mixture is stirred for 1 hour and then filtered. 400 ml of methanol are then added to the aqueous solution and the precipitate is filtered off. After drying, 11.5 g of the expected product are obtained. Melting point >300° C.

| Elemental analysis | | | | | | |
|---|---|---|---|---|---|---|
| Calculated | C% | 28.6 | H% | 5.57 | N% | 3.7 |
| Found | | 28.1 | | 5.84 | | 3.46 |

EXAMPLE 10

Monosodium salt of 1-methylamino-4-(4-chlorophenylthio)-butylidene-1,1-diphosphonic acid (SR 43140 A).

I R₁ = 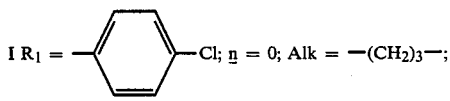 Cl; $\underline{n}$ = 0; Alk = —(CH₂)₃—;

R₂ = CH₃; R₃ = H

A mixture of 20 g of N-methyl-4-(4-chlorophenylthio)butyramide, 10 ml of phosphorus trichloride, 13 g of phosphorous acid and 100 ml of dimethoxyethane is heated under reflux for 3 hours. It is then left to stand for 12 hours at ambient temperature and the crystals are filtered off. They are washed with methanol and then with acetone. Weight: 25 g. The acid obtained in this way is suspended in 250 ml of water, 15 g of sodium acetate are then added and the mixture is heated under reflux for 3 hours. After cooling, the solid is filtered off, washed with methanol and then with ether and dried. Weight: 24.25 g; melting point >260° C.

| | Elemental analysis | | | | | |
|---|---|---|---|---|---|---|
| Calculated | C% | 32.09 | H% | 4.16 | N% | 3.40 |
| Found | | 32.09 | | 3.85 | | 3.46 |

EXAMPLES 11 TO 22

The products (I), n=0, collated in Table 1 are obtained by following the procedure of Example 10 but varying the starting amide. When the acid does not crystallize on cooling of the reaction mixture, the latter is evaporated by dryness to vacuo and the residue is taken up in water.

To prepare the sodium salts, the sodium acetate can be replaced with sodium hydroxide.

TABLE 1

| Ex. No. | SR code no. | R₁ | Alk | R₂ | R₃ | Acid or Salt melting point °C. Analysis (calculated value) |
|---|---|---|---|---|---|---|
| 11 | 43 141 | Cl—C₆H₄— | (CH₂)₃ | —CH₃ | —CH₃ | acid m.p.: 202<br>C: 35.70 (35.63)<br>H: 4.99 (4.73)<br>N: 3.47 (3.43) |
| 12 | 43 162 A | Cl—C₆H₄— | (CH₂)₃ | H | —C₆H₄—CH₃ | disodium salt m.p. > 260 with 1H₂O<br>C: 38.70 (38.50)<br>H: 3.94 (4.19)<br>N: 2.65 (2.63) |
| 13 | 43 164 | " | " | H | —(CH₂)₅CH₃ | acid m.p.: 222<br>C: 41.42 (41.79)<br>H: 6.37 (6.14)<br>N: 2.99 (3.04) |
| 14 | 43 163 | " | " | | —(CH₂)₅— | acid m.p.: 208<br>C: 40.61 (40.59)<br>H: 5.68 (5.45)<br>N: 3.11 (3.15) |
| 15 | 43 175 A | " | " | H | —C₆H₄—Cl | disodium salt m.p. > 260 with 3H₂O<br>C: 32.80 (32.95)<br>H: 3.56 (3.94)<br>N: 2.26 (2.40) |
| 16 | 43 176 | " | " | H | —CH₂—C₆H₅ | acid m.p.: 194 with 2H₂O<br>C: 41.64 (41.60)<br>H: 4.53 (4.82)<br>N: 2.76 (2.79) |
| 17 | 43 299 B | H₃C—C₆H₄— | CH₂ | H | —CH(CH₃)₂ | disodium salt m.p. > 260 with 2H₂O<br>C: 32.03 (32.07)<br>H: 5.05 (5.15)<br>N: 3.09 (3.11) |
| 18 | 43 404 A | CH₃—CH₂— | (CH₂)₄ | H | —CH₃ | monosodium salt m.p. > 300<br>C: 28.34 (28.00)<br>H: 5.55 (5.87)<br>N: 4.26 (4.08) |
| 19 | 43 376 A | CF₃—C₆H₄— | (CH₂)₂ | H | —CH₃ | monopotassium salt m.p. > 300 with 1H₂O<br>C: 28.36 (28.39)<br>H: 3.24 (3.68)<br>N: 2.99 (3.01) |

TABLE 1-continued

| Ex. No. | SR code no. | R₁ | Alk | R₂ | R₃ | Acid or Salt melting point °C. Analysis (calculated value) |
|---|---|---|---|---|---|---|
| 20 | 43 368 A | cyclohexyl | (CH₂)₅ | H | —CH₃ | dipotassium salt m.p. > 300 with 2H₂O C: 31.47 (31.13) H: 5.89 (6.22) N: 2.76 (2.79) |
| 21 | 43 369 A | H₃C—C₆H₄— | —CH—CH₂— \| CH₃ | H | —CH₂CH₂CH₃ | disodium salt m.p.: 260 with 1H₂O C: 36.96 (36.61) H: 5.69 (5.48) N: 3.07 (3.05) |
| 22 | 43 354 A | pyridyl | (CH₂)₄ | H | —CH₃ | disodium salt m.p. > 260 with ½H₂O C: 31.20 (31.38) H: 4.40 (4.45) N: 6.62 (6.65) |

EXAMPLE 23

4-Phenylthio-1-ureidobutylidene-1,1-diphosphonic acid (SR 43142).

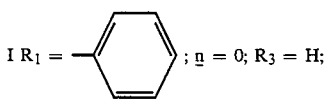

I R₁ = phenyl ; $\underline{n}$ = 0; R₃ = H;

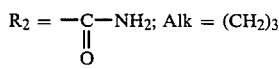

R₂ = —C—NH₂; Alk = (CH₂)₃
       ‖
       O 10 g of 1-amino-4-phenylthiobutylidene-1,1-diphosphonic acid (Example 5) are introduced into 45 g of molten urea (150° C.), with stirring, and this temperature is maintained for 90 minutes. The reaction mixture is poured into 500 ml of acetone and the insoluble material is filtered off hot. It is treated again with 1 liter of acetone and filtered off. The insoluble material is dissolved in water and transferred to a column of sulfonic acid resin activated with 2N HCl beforehand. After evaporation of the water, a solid is obtained, which is triturated with methylene chloride. This finally gives 5.6 g of a colorless solid. Melting point: 125°–130° C.

| Elemental analysis | | | | | | | |
|---|---|---|---|---|---|---|---|
| Calculated | C% | 34.38 | H% | 4.72 | N% | 7.29 |
| Found | | 34.10 | | 4.74 | | 7.27 |

EXAMPLE 24

4-(4-Chlorophenylsulfinyl)-1-methylaminobutylidene-1,1-diphosphonic acid (SR 43264).

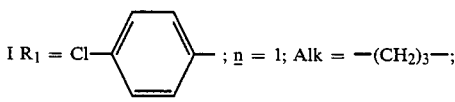

I R₁ = Cl—C₆H₄— ; $\underline{n}$ = 1; Alk = —(CH₂)₃—;

R₂ = H; R₃ = CH₃

A mixture of 8.5 g of N-methyl-4-(4-chlorophenylsulfinyl)butyramide, 4 ml of phosphorus trichloride, 8 g of phosphorous acid and 50 ml of 1,2-dimethoxyethane is heated under reflux for 3 hours. The solvent is evaporated off to dryness in vacuo and the residue is taken up with boiling water. The solid is filtered off and washed with water and then with methanol. This gives 6 g of a solid; melting point >260° C.

| Elemental analysis - with H₂O | | | | | | |
|---|---|---|---|---|---|---|
| Calculated | C% | 31.27 | H% | 4.76 | N% | 3.30 |
| Found | | 31.28 | | 4.78 | | 3.32 |

EXAMPLE 25

Monosodium salt of 1-methylamino-4-(4-methylphenylsulfonyl)propylidene-1,1-diphosphonic acid (SR 43370 A).

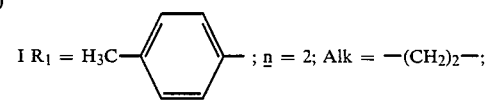

I R₁ = H₃C—C₆H₄— ; $\underline{n}$ = 2; Alk = —(CH₂)₂—;

R₂ = H; R₃ = CH₃

A mixture of 9.5 g of N-methyl-3-(4-methylphenylsulfonyl)propionamide, 9 ml of phosphorus trichloride, 6 g of phosphorous acid and 50 ml of 1,2-dimethoxyethane is heated under reflux for 3 hours. It is concentrated to dryness in vacuo and the residue is then taken up in 200 ml of boiling water. After cooling, the solution is filtered and 20 g of sodium acetate are added. The mixture is left for 12 hours and the solid is filtered off and washed twice with water and then with acetone. The crude sodium salt is suspended in 100 ml of distilled water. 1 ml of concentrated hydrochloric acid is added and the mixture is heated under reflux for 30 minutes. After cooling, the precipitate is filtered off and washed with water and methanol. After drying, 3.6 g of the expected product are obtained; melting point >300° C.

| Elemental analysis | | | | | | |
|---|---|---|---|---|---|---|
| Calculated | C% | 32.12 | H% | 4.41 | N% | 3.41 |
| Found | | 31.79 | | 4.21 | | 3.39 |

The compounds according to the invention are advantageously used as antiinflammatory and antirheumatic drugs and their pharmacological properties were demonstrated in the following manner:

"IN VIVO" STUDY: ADJUVANT ARTHRITIS

The injection of rats with mycobacterium causes a polyarthritis and in certain respects resembles human rheumatoid arthritis.

Protocol

A suspension of Mycobacterium tuberculosis (0.4 mg) in paraffin oil (0.05 ml) is injected intradermally into the tail of male Sprague-Dawley rats having a mean weight of 150 g.

After 15 days, the animals exhibiting the most marked symptoms of arthritis are selected. These rats are divided into 2 groups of 14 animals.

The animals of the 1st group are treated 6 days/week for 3 weeks;
either subcutaneously with doses ranging from 0.32 $\mu$mol to 32 $\mu$mol/kg/day,
or orally with a dose of 0.16 mmol/kg/day. The second group receives placebo and serves as the control group.

After 3 weeks of treatment, half the animals in each group are sacrificed; the other half are kept for 2 weeks without treatment and then sacrificed in turn.

After the animals have been sacrificed, the right rear paw is removed at the tribiotarsal joint and then weighed. The mean and the standard error of the weights are determined for each half-group.

The activity of the product is expresed as the percentage variation in the mean weight of the paws of the treated arthritic rats relative to that of the arthritic paws of the untreated rats (control rats).

The results obtained with various products of the invention are collated in Table 2 below. For each of the products tested, the therapeutic activity is expressed as the percentage inhibition of the weight of the paw after 3 weeks of treatment.

For some products, the result obtained after 5 weeks, i.e. 3 weeks of treatment followed by 2 weeks without treatment, have also been shown.

| Product SR No. | Method of Administration | % Inhibition of the weight of the paw | |
|---|---|---|---|
| | | at the end of the treatment (3 weeks) | 2 weeks after the end of the treatment |
| 42 509 A | oral | 17 | 22 |
| 42 683 A | " | 9 | 13 |
| 42 708 A | " | 28 | 22 |
| 42 709 A | " | 0 | 14 |
| 42 710 A | " | 19 | 7 |
| 42 718 A | " | 35 | 16 |
| 43 140 A | subcutaneous | 52 | |
| 43 141 | " | 36 | |
| 43 142 | " | 37 | |
| 43 162 A | " | 49 | |
| 43 163 | " | 35 | |
| 43 164 | " | 35 | |
| 43 175 A | " | 22 | |
| 43 176 | " | 52 | |
| 43 264 | " | 29 | |
| 43 299 B | " | 25 | |
| 43 304 A | " | 30 | |
| 43 354 A | " | 44 | |
| 43 368 A | " | 20 | |
| 43 369 A | " | 38 | |
| 43 370 A | " | 32 | |
| 43 376 A | " | 38 | |

These results show that the products according to the invention have a substantial antirheumatic activity after 3 weeks of treatment.

It should be noted that this activity is maintained at a high level and sometimes even increases 2 weeks after the end of the treatment.

Moreover, the products according to the invention are of low toxicity.

They can be used in human therapy for the treatment of complaints due to inflammatory phenomena and especially for the treatment of arthritic conditions. In particular, the compounds according to the invention can be used in the treatment of rheumatoid polyarthritis.

The invention also relates to the pharmaceutical compositions containing a derivative according to the invention as the active ingredient, in association with a pharmaceutically acceptable vehicle.

The compositions according to the invention can be presented in forms suitable for oral, endorectal and parenteral administration.

In particular, these forms can be capsules or tablets containing a quantity of active principle of 10 to 500 mg/unit.

The daily dosage of these products for an adult can be of the order of 100 mg to 5 g, divided up into several individual doses.

The following galenical composition can be given as an example:

| Capsules | |
|---|---|
| SR 42708 A | 200 mg |
| Aerosil | 1 mg |
| Magnesium stearate | 3 mg |
| Starch STA RX 1500 | 96 mg |
| | 300 mg |

We claim:

1. A methylenediphosphonic acid derivative of the formula:

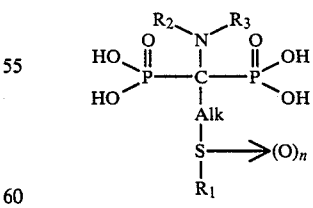

wherein:
R$_1$ represents C$_5$–C$_7$ cycloalkyl, phenyl unsubstituted or monosubstituted or polysubstituted by a member selected from amongst halogen, C$_1$–C$_6$ alkyl or trifluoromethyl; or pyridyl
Alk denotes linear or branched C$_1$–C$_6$ alkylene;
R$_2$ represents hydrogen, C$_1$–C$_6$ alkyl or —CONH$_2$;

R3 represents hydrogen, $C_1$–$C_6$ alkyl, benzyl or phenyl unsubstituted or substituted by a member selected from amongst chlorine or methyl;

$R_2$ and $R_3$, taken together, represent $(CH_2)_m$, in which m is 4 or 5; and n is 0, 1 or 2;

and salts thereof with pharmaceutically acceptable inorganic or organic bases.

2. A methylenediphosphonic acid derivative according to claim 1, wherein $R_1$ is p-chlorophenyl, Alk is $(CH_2)_3$, $R_2$ is H and $R_3$ is benzyl.

3. A methylenediphosphonic acid derivative of the formula:

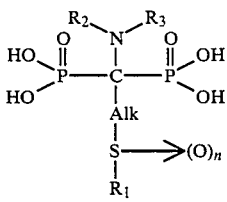

wherein:

$R_1$ represents $C_1$–$C_6$ alkyl;

Alk denotes linear or branched $C_1$–$C_6$ alkylene;

$R_2$ represents hydrogen, $C_1$–$C_6$ alkyl or —$CONH_2$;

$R_3$ represents hydrogen, $C_1$–$C_6$ alkyl, benzyl or phenyl unsubstituted or substituted by a member selected from amongst chlorine or methyl;

$R_2$ and $R_3$, taken together, represent $(CH_2)_m$, in which m is 4 or 5; and n is 1;

and salts thereof with pharmaceutically acceptable inorganic or organic bases.

4. A method for the treatment of rheumatism or rheumatoid polyarthritis which comprises administering to an animal in need thereof an antirheumatic effective amount of methylenediphosphonic acid derivative of the formula:

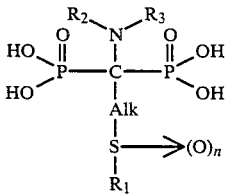

wherein:

$R_1$ represents $C_1$–$C_6$ alkyl or $C_5$–$C_7$ cycloalkyl; or $R_1$ represents phenyl unsubstituted or monosubstituted or polysubstituted by halogen, $C_1$–$C_6$ alkyl or trifluoromethyl, or pyridal;

Alk denotes linear or branched $C_1$–$C_6$ alkylene;

$R_2$ represents hydrogen, $C_1$–$C_6$ alkyl or —$CONH_2$;

$R_3$ represents hydrogen, $C_1$–$C_6$ alkyl, benzyl or phenyl unsubstituted or substituted by a member selected from amongst chlorine or methyl;

$R_2$ and $R_3$, taken together, represent $(CH_2)_m$, in which m is 4 or 5; and n is 0, 1 or 2;

and salts thereof with pharmaceutically acceptable inorganic or organic bases.

5. A pharmaceutical composition having an antirheumatic action, which comprises, as the active ingredient, a methylenediphosphonic acid derivative of the formula:

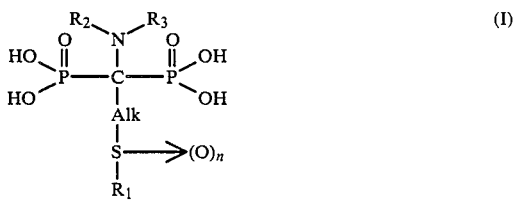

wherein:

$R_1$ represents $C_5$–$C_7$ cycloalkyl, phenyl unsubstituted or monosubstituted or polysubstituted by halogen, $C_1$–$C_6$ alkyl or trifluoromethyl, or pyridyl;

Alk denotes linear or branched $C_1$–$C_6$ alkylene;

$R_2$ represents hydrogen, $C_1$–$C_6$ alkyl or —$CONH_2$;

$R_3$ represents hydrogen, $C_1$–$C_6$ alkyl, benzyl or phenyl unsubstituted or substituted by a member selected from amongst chlorine or methyl;

$R_2$ and $R_3$, taken together, represent $(CH_2)_m$, in which m is 4 or 5; and n is 0, 1 or 2;

or one of the pharmaceutically acceptable salts of the said derivative with organic or inorganic bases, in association with a pharmaceutically acceptable vehicle.

6. A composition as claimed in claim 5, having 10 to 500 mg of active ingredient.

7. A pharmaceutical composition having an antirheumatic action, which comprises as the active ingredient, and effective amount of a methylenediphosphonic acid derivative of the formula:

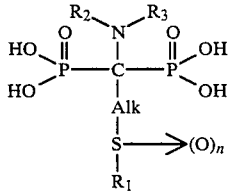

wherein:

$R_1$ represents $C_1$–$C_6$ alkyl;

Alk denotes linear or branched $C_1$–$C_6$ alkylene;

$R_2$ represents hydrogen, $C_1$–$C_6$ alkyl or —$CONH_2$;

$R_3$ represents hydrogen, $C_1$–$C_6$ alkyl, benzyl or phenyl unsubstituted or substituted by a member selected from amongst chlorine or methyl;

$R_2$ and $R_3$, taken together, represent $(CH_2)_m$, in which m is 4 or 5; and n is 1;

or one of the pharmaceutically acceptable salts of the said derivative with organic or inorganic bases; in association with a pharmaceutically acceptable vehicle.

8. A composition as claimed in claim 7, having 10 to 500 mg of active ingredient.

* * * * *